United States Patent
Tate et al.

(10) Patent No.: US 9,625,373 B2
(45) Date of Patent: Apr. 18, 2017

(54) SPECTROSCOPIC ANALYSIS AND CONTROL

(75) Inventors: James D. Tate, Lake Jackson, TX (US); Christopher J. Reed, Port Allen, LA (US); Christopher H. Domke, Rosharon, TX (US); Linh Le, Lake Jackson, TX (US); Mary Beth Seasholtz, Sanford, MI (US); Andy Weber, Brazoria, TX (US); Charles Lipp, Lake Jackson, TX (US)

(73) Assignee: Dow Global Technology LLC, Midland, MI (US)

( * ) Notice: Subject to any disclaimer, the term of this patent is extended or adjusted under 35 U.S.C. 154(b) by 1928 days.

(21) Appl. No.: 11/885,212

(22) PCT Filed: Mar. 22, 2006

(86) PCT No.: PCT/US2006/010358
§ 371 (c)(1),
(2), (4) Date: Jun. 2, 2008

(87) PCT Pub. No.: WO2006/104796
PCT Pub. Date: Oct. 5, 2006

(65) Prior Publication Data
US 2009/0216462 A1    Aug. 27, 2009

Related U.S. Application Data

(60) Provisional application No. 60/666,299, filed on Mar. 29, 2005.

(51) Int. Cl.
*G01N 33/48* (2006.01)
*G01N 33/50* (2006.01)
(Continued)

(52) U.S. Cl.
CPC ......... *G01N 21/3504* (2013.01); *G01N 21/39* (2013.01); *G06F 17/10* (2013.01); *G06F 17/11* (2013.01); *G06F 19/12* (2013.01)

(58) Field of Classification Search
None
See application file for complete search history.

(56) References Cited

U.S. PATENT DOCUMENTS 5,206,701 A * 4/1993 Taylor et al. .................. 356/325
5,684,580 A * 11/1997 Cooper et al. ................ 356/301
(Continued)

FOREIGN PATENT DOCUMENTS

CN    1154473 A    7/1997

OTHER PUBLICATIONS

Wheeler et al. Lower cost, higher value on-line analyzer technology for application in the manufacture of ethylene. ISA TECH/EXPO Technology Update Conference Proceedings, 1997, Part 1/2 of 5, pp. 225-238.*

(Continued)

*Primary Examiner* — Russell S Negin

(57) ABSTRACT

Apparatus for spectroscopic analysis which includes a tunable diode laser spectrometer having a digital output signal and a digital computer for receiving the digital output signal from the spectrometer, the digital computer programmed to process the digital output signal using a multivariate regression algorithm. In addition, a spectroscopic method of analysis using such apparatus. Finally, a method for controlling an ethylene cracker hydrogenator.

4 Claims, 4 Drawing Sheets

(51) Int. Cl.
*G01N 21/3504* (2014.01)
*G06F 17/11* (2006.01)
*G06F 17/10* (2006.01)
*G01N 21/39* (2006.01)
*G06F 19/12* (2011.01)

(56) References Cited

U.S. PATENT DOCUMENTS

| | | | |
|---|---|---|---|
| 5,830,133 | A | 11/1998 | Osten et al. |
| 5,957,858 | A | 9/1999 | Micheels et al. |
| 6,615,142 | B1 | 9/2003 | Hovde |
| 2003/0104767 | A1 | 6/2003 | Chilton |
| 2003/0134427 | A1 | 7/2003 | Roller et al. |
| 2004/0191712 | A1 | 9/2004 | Thomson et al. |

OTHER PUBLICATIONS

Wheeler et al., Abstract of [Lower cost, higher value on-line analyzer technology for application in the manufacture of ethylene. ISA TECH/EXPO Technology Update Conference Proceedings, 1997, Part 1/2 of 5, pp. 225-238.], obtained from DIALOG on Aug. 19, 2010 for proof of 1997 date.*

Crosson et al. Stable isotope ratios using cavity ring-down spectroscopy: determination of 13C/12C for carbon dioxide in human breath. Analytical Chemistry, 2002, vol. 74, pp. 2003-2007.*

Definition of "Noble Gas." Chambers 21st Century Dictionary, 2001. Retrieved on Aug. 16, 2010 online <<http://www.credoreference.com/entry/chambdict/noble_gas>>.*

Yang et al. Comparison of partial least squares regression and multi-layer neural networks for quantification of nonlinear systems and application to gas phase Fourier transform infrared spectra. Analyticc Chimica Acta, 2003, vol. 489, pp. 125-136.*

Baer et al. Sensitive absorption measurements in the near-infrared region using off-axis integrated-cavity-output spectroscopy. Applied Physics B: Lasers and Optics, vol. 75, 2002, pp. 261-265.*

Bouzidi, Moncef et al., Adjoint Spectrum I: an Algorithm to Extract Target Spectra Under Spectral Interferences for Use in On-Line Spectrometry, Japanese Journal of Applied Physics, 1992, p. 4071-8031,12A, (Abstract provided).

Gupta, Manish et al, Sensors and Automation, Cavity-Enhanced Gas Analyzer for Process Control Applications, U.S. Department of Energy Website, CPS No. 17139, Jun. 2004.

Slice, Dennis E., et al, A Glossary for Geometric Morphometrics (part 2), State University of New York at Stony Brook, NY, Revised Nov. 24, 1998 by F. James Rohlf.

Regression Analysis—Wikipedia, the free encyclopedia, http://wikipedia.org/wiki/Regression_analysis, retrieved Jan. 23, 2007.

Bakhirkin, Yury A., et al., Mid-infrared quantum cascade laser based off-axis integrated cavity output spectroscopy for biogenic nitric oxide detection, Applied Optics, Apr. 2004, vol. 43, No. 11, p. 2257.

Mackay et al., "Tunable Diode Laser Systems for Trace Gas Monitoring", Measurement of Atmospheric Gases, 1991, vol. 1433, pp. 104-119.

Silver et al., "Miniature Gas Sensor for Monitoring Biological Space Environments", Proceedings of SPIE, 2002, vol. 4817, pp. 82-87.

"Multivariate Calibration and Prediction" in: K.R. Beebe et al.: "Chemometrics: A Practical Guide" 1998, John Wiley & Sons, Inc., pp. 183-188 and 337-339.

\* cited by examiner

SPECTROSCOPIC ANALYSIS AND CONTROL

CROSS REFERENCE TO RELATED APPLICATIONS

This application is a 371 of PCT/US2006/010358 filed 22 Mar. 2007, which claims the benefit of U.S. Provisional Application Ser. No. 60/666,299, filed 29 Mar. 2005.

The instant invention was made under Department of Energy contract DE-FC07-0211D14428 under which the Government has certain interests in the instant invention.

BACKGROUND OF THE INVENTION

Tunable diode laser spectroscopic analysis of gaseous samples is known, see, for example, U.S. Pat. No. 6,615,142. The method of the '142 patent relies on a computation with the assumption that the sample spectrum can be fitted as a linear combination of its pure constituents. However, when the concentration of the components of interest is relatively low in the sample matrix, then, for example, the computation of the '142 patent fails to accurately determine the concentration of the components of interest. For example, when the sample matrix is the gaseous stream from an ethylene cracker acetylene hydrogenator and the component to be analyzed in the sample is acetylene at a concentration of about 1 part per million, then the computation of the '142 patent fails to accurately estimate the concentration of the relatively low concentration of acetylene. It would be an advance in the art if a tunable diode laser based spectroscopic method could be discovered that solved the above-stated problems of the prior art.

The determination of such low levels of acetylene is important for ethylene cracker hydrogenators. An ethylene cracker produces undesirable acetylene along with the desired ethylene and propylene. The purification system does not remove the undesired acetylene. Therefore, a hydrogenator is used to hydrogenate the acetylene to ethylene. Ethylene cracker hydrogenators are generally of two types. The "front end" hydrogenator is fed directly from the cracker and contains hydrogen as made in the cracker. The "back end" hydrogenator is usually fed from a purification system which receives its feed from the cracker and must add hydrogen to the reactor because it was removed in a prior purification step. The hydrogenator is fed a controllably heated gaseous stream from the cracker or from the purifier.

The heart of an ethylene cracker hydrogenator is a bed of catalytic material which catalytically reacts the acetylene with the hydrogen. In the art, filter photometry is typically used to determine acetylene in the range of from, for example, 0.3 to 1% in the feed stream while gas chromatography is typically used to determine acetylene in the range of, for example, about 1 part per million in the outlet stream from the hydrogenator. There is little dissatisfaction with the filter photometry analysis of the inlet stream for acetylene. However, gas chromatography does not provide sufficiently rapid analysis of the outlet stream for acetylene to prevent, for example, off-spec product or a thermal run-away of the hydrogenator system. It would be an advance in the art if a method could be discovered that solved the above-stated problems of the prior art ethylene cracker hydrogenator control systems.

SUMMARY OF THE INVENTION

The instant invention is a solution to the above-stated problems. The instant invention is a chemical analysis method for determining the concentration of a gaseous component of interest in a sample gas comprising a gaseous matrix, comprising seven steps. The first step is to direct light from a tunable diode laser through an inert gas contained in a sample cell over a selected range of n wavelengths to a light detector to produce a range of baseline signals $I_0n$ from the light detector, the inert gas being essentially transparent over the selected range of n wavelengths, The second step is to digitize the range of baseline signals $I_0n$ from the light detector. The third step is to store the digitized baseline signals $I_0n$ in a digital computer. The fourth step is to direct light from the tunable diode laser through the sample gas contained in the sample cell over the selected range of n wavelengths to the light detector to produce a range of sample signals $I_Sn$ from the light detector. The fifth step is to digitize the range of sample signals $I_Sn$ from the light detector; (f) storing the digitized sample signals $I_Sn$ in a digital computer. The sixth step is to calculate a spectrum in the digital computer according to the equation $I(n)=(I_0n-I_Sn)/I_0n$. The seventh step is to produce a signal from the computer indicative of the concentration of the gaseous component of interest by using spectra of a known concentration of the component of interest in the inert gas stored digitally in the computer, the spectrum of step (g) and a multivariate regression algorithm programmed in the computer.

In another embodiment the instant invention is an apparatus for spectroscopic analysis, comprising: (a) a tunable diode laser spectrometer having a digital output signal; (b) a digital computer for receiving the digital output signal from the spectrometer, the digital computer programmed to process the digital output signal using a multivariate regression algorithm. The tunable diode laser spectrometer may include but is not limited to the use of long-path gas cell (Herriot cell) and or a detector based on a Quartz-enhanced photo-acoustic device (See e.g. WO 03/104767 A2).

In yet another embodiment, the instant invention is an improved process for controlling an ethylene cracker hydrogenator, the gaseous stream being fed to the hydrogenator being controllably heated, the acetylene concentration of the outlet stream from the hydrogenator being determined by a chemical analysis method so that the hydrogenator can be controlled, wherein the improvement comprises the use of the above discussed method of the instant invention to determine the concentration of acetylene in the outlet stream from the hydrogenator.

In yet another embodiment, the instant invention is an improved process for controlling an ethylene cracker hydrogenator, the hydrogen stream being fed to the hydrogenator being controlled, the acetylene concentration of the outlet stream from the hydrogenator being determined by a chemical analysis method so that the hydrogenator can be controlled, wherein the improvement comprises the use of the above discussed method of the instant invention to determine the concentration of acetylene in the outlet stream from the hydrogenator.

DETAILED DESCRIPTION

Figure 1:
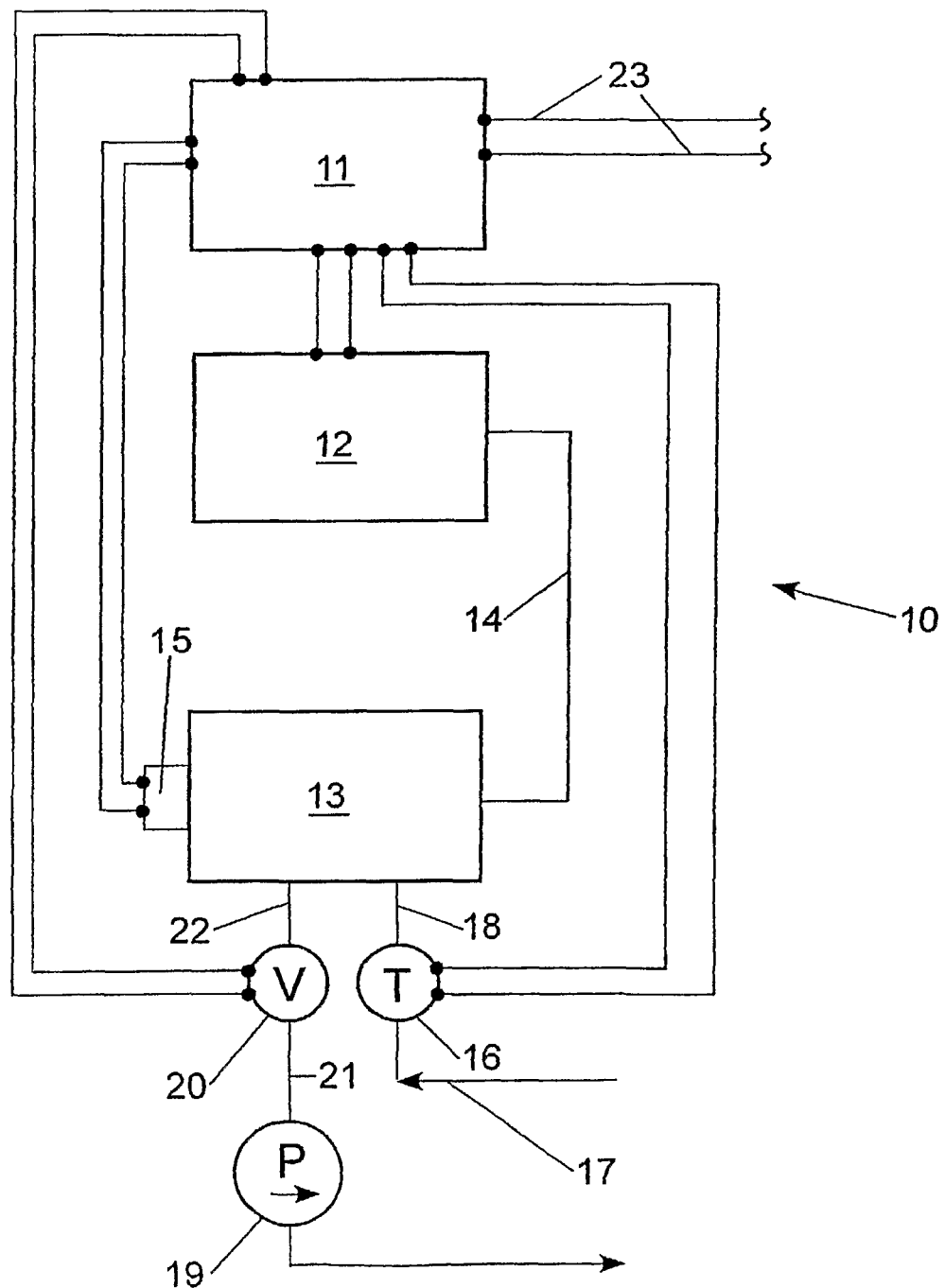
FIG. 1 is a schematic drawing of a preferred apparatus embodiment of the instant invention.

Referring now to FIG. 1, therein is shown a schematic drawing of a preferred apparatus embodiment 10 of the instant invention including hardware 11 comprising a CPU/laser temperature and current control/detector electronics/user interface and display. The system 11 is in electrical communication with tunable diode laser, laser mount, heat sink and thermoelectric control system 12. Light from the system 12 is directed to a one half liter internal volume Off-Axis Integrated Cavity Output Spectrometry (ICOS) sample cell 13 from Los Gatos Research, Mt. View Calif., by way of an optical fiber 14. The light is detected by light detector in electrical communication with the system 11. The output stream from an ethylene cracker hydrogenator is directed through pressure transducer 16 to cell 13 by way of tubing 17 and 18. The pressure transducer 16 is in electrical communication with the system 11 so that the system 11 can determine the pressure of the gas in the cell 13. A vacuum pump 19 is in fluid communication with a flow control valve 20 by way of tubing 21. The flow control valve 20 is in fluid communication with the cell 13 by way of tubing 22. The flow control valve 20 is in electrical communication with the system 11 so that the pressure of the gas in the cell 13 can be controlled at a pressure determined by way of the transducer 16 by controlling the valve 20.

The apparatus 10 can be used to determine the concentration of acetylene in a gas stream from an ethylene cracker hydrogenator by a method of the instant invention which comprises seven steps. The first step is to direct light from the tunable diode laser 12 through an inert gas contained in the sample cell 13 (by way of tubing 17 and 18) over a selected range of n wavelengths to the light detector 15 to produce a range of baseline signals $I_0 n$ from the light detector 15 to the system 11, the inert gas being nitrogen which is essentially transparent over the selected range of n wavelengths. The second step is to digitize the range of baseline signals $I_0 n$ from the light detector 15 in the system 11. The third step is to store the digitized baseline signals $I_0 n$ in the digital computer portion of system 11. The fourth step is to direct light from the tunable diode laser 12 through the gas stream from the ethylene cracker by way of the tubing 17 and 18, the gas contained in the sample cell 13, over the selected range of n wavelengths to the light detector 15 to produce a range of sample signals $I_S n$ from the light detector 15 to the system 11. The fifth step is to digitize the range of sample signals $I_S n$ from the light detector 15 in the system 11. The sixth step is to store the digitized sample signals $I_S n$ in the digital computer portion of the system 11. The seventh step is to calculate a spectrum in the digital computer according to the equation $I(n)=(I_0 n - I_S n)/I_0 n$; (h) producing a signal to wires 23 from the computer indicative of the concentration of the acetylene by using spectra of a known concentration of acetylene in nitrogen, such standardizing spectra stored digitally in the computer, the spectrum of step (g) and a multivariate regression algorithm programmed in the computer. The standardizing spectra of acetylene, methylacetylene and ethylene are obtained by substituting a standard gas mixture of each for the gas stream from the ethylene cracker hydrogenator in the above procedure.

The specific components used in the apparatus 10 are not critical in the instant invention and can be obtained, for example, from Analytical Specialties, Inc., Houston Tex. The specific multivariate regression algorithm used in the system 11 of the apparatus 10 is not critical in the instant invention and can be obtained, for example, from Eigenvector Research, Inc., Manson Wash.

The flow rate of gas into the cell 13 is preferably about 1.5 liter per minute so that an analysis can reported about every 15 seconds. Preferably, a number of spectra are averaged over the 15 seconds to increase the precision of the determination. Although not critical in the full scope of the instant invention, when the instant invention is used to analyze the gas stream from an ethylene cracker hydrogenator, then it is highly preferable to control the pressure of the gas in the cell 13 between 25 and 150 and even more preferably between 75 and 125 torr. In the following example, such pressure is about 100 torr.

The term "inert gas" used in step (a) of the method of the instant invention refers to a gas that is essentially transparent over the selected range of wavelengths. The term "inert gas" as used herein does not refer to the reactivity of the gas. The specific inert gas used in step (a) of the method of the instant invention is not critical as long as such gas is essentially transparent over the selected range of wavelengths. Nitrogen is often a preferred inert gas in the instant invention. However, gases such as helium and argon can also be used, and, of course, mixtures of such inert gases can be used if desired.

Figure 4:
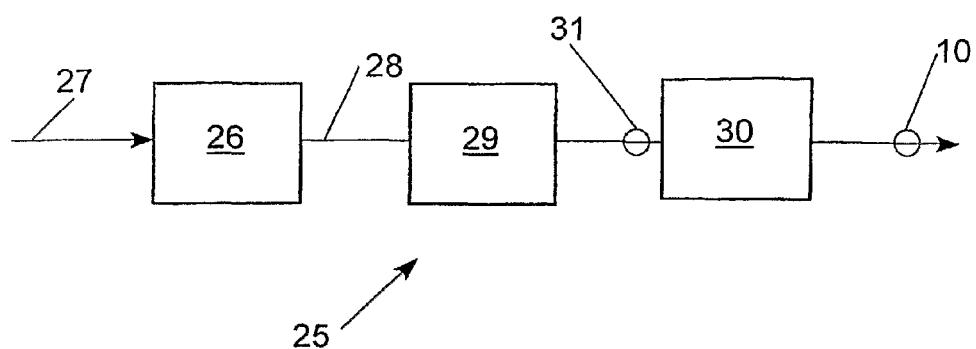
FIG. 4 shows a schematic drawing of the apparatus of FIG. 1 for controlling a "front end" ethylene cracker hydrogenator.

Referring now to FIG. 4, therein is shown a schematic view of a "front end" hydrogenation process 25. The process 25 includes a steam cracker 26. The steam cracker 26 is fed a mixture 27 comprising steam and a hydrocarbon such as naphtha. The output stream 28 is fed through a heater 29 to a catalytic hydrogenator 30. The apparatus 10 of FIG. 1 is used to analyze the output stream from the hydrogenator 30 for acetylene. The output from the apparatus 10 is used in a feedback or feed forward control system to, for example, control the temperature of the input stream to hydrogenator 30 by controlling heater 29. Preferably, a filter photometer 31 such as an ABB Mulitwave brand photometer) is used to determine the concentration of acetylene in the stream flowing into the hydrogenator 30.

Figure 5:
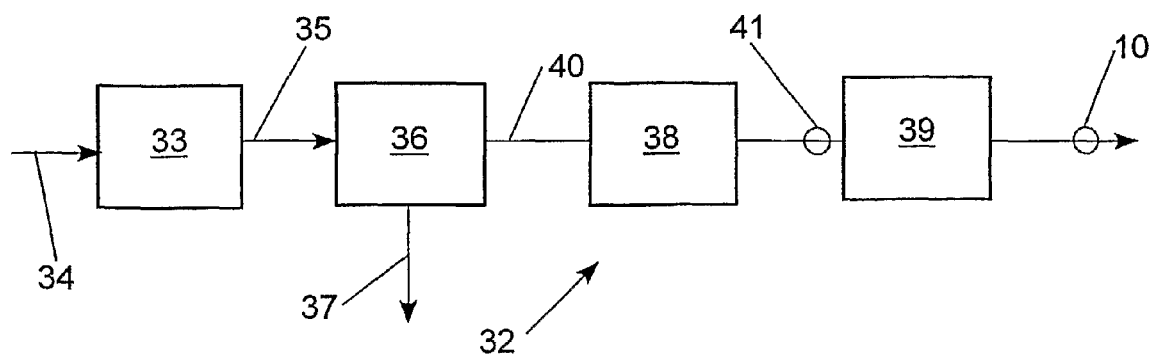
FIG. 5 shows a schematic drawing of the apparatus of FIG. 1 for controlling a "back end" ethylene cracker hydrogenator.

Referring now to FIG. 5, therein is shown a schematic view of a "back end" hydrogenation process 32. The process 32 includes a steam cracker 33. The steam cracker 33 is fed a mixture 34 comprising steam and a hydrocarbon such as natural gas liquids. The output stream 35 is fed to a separation system 36 to remove impurities 37. The output of the separation system 36 is enriched in ethylene and is directed through a heater 38 to a catalytic hydrogenator 39. The apparatus 10 of FIG. 1 is used to analyze the output stream from the hydrogenator 39 for acetylene. Hydrogen 40 is added to the stream flowing through the heater 38 to provide hydrogen for the hydrogenation of acetylene that occurs in the hydrogenator 39. The output from the apparatus 10 is used in a feedback or feed forward control system to, for example, control the temperature of the input stream to hydrogenator 30 by controlling heater 29 and the flow rate of hydrogen 40. Preferably, a filter photometer 41 (such as an ABB Mulitwave brand photometer) is used to determine the concentration of acetylene in the stream flowing into the hydrogenator 39.

EXAMPLE

Figure 2:
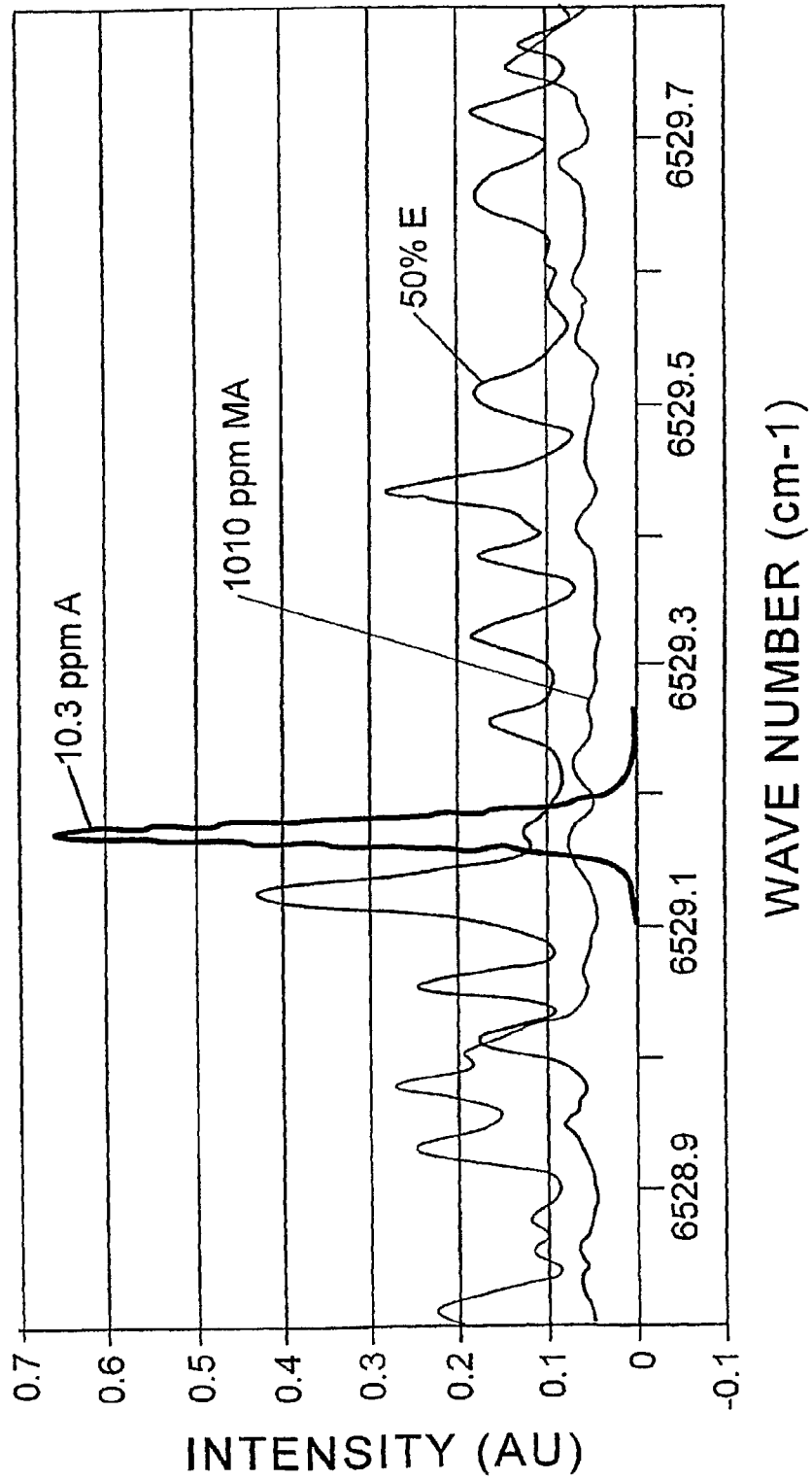
FIG. 2 shows overlaid individual spectra of pure acetylene at 10.3 ppm in nitrogen, of pure methylacetylene at 1010 ppm in nitrogen and of pure ethylene at 50% in nitrogen.

The apparatus 10 of FIG. 1 is installed in the system 25 shown in FIG. 4. Standardizing spectra are obtained for acetylene over a concentration range of from 0.5 to 10 parts per million. Standardizing spectra are obtained for methylacetylene over a concentration range of from 500 to 10,000 parts per million. Standardizing spectra are obtained for ethylene over a concentration range of from 25 to 75 percent. FIG. 2 shows some of the standardizing spectra.

The following three mixtures are prepared:
(1) 8 ppm acetylene; 920 ppm methylacetylene; 40 percent ethylene;
(2) 1.5 ppm acetylene; 890 ppm methylacetylene; 39 percent ethylene; and
(3) 1.5 ppm acetylene; 5070 ppm methylacetylene; 40 percent ethylene.

Figure 3:
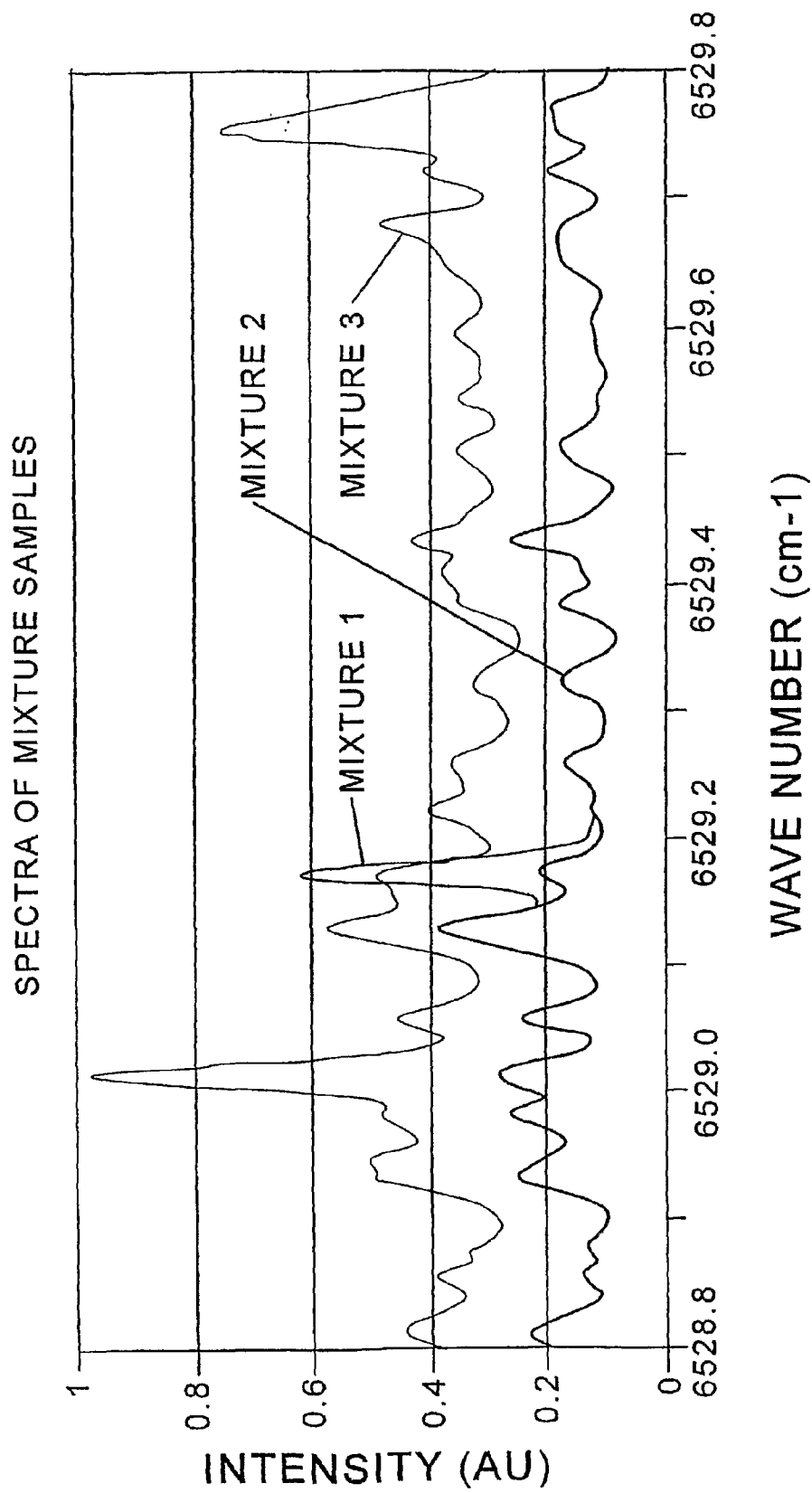
FIG. 3 shows overlaid spectra of the gaseous stream from an ethylene cracker hydrogenator.

The above three mixtures are then analyzed using the system described above in reference to FIG. 1. FIG. 3 shows the spectra for each mixture. The instant invention reports the following results:
(1) 8 ppm acetylene; 1000 ppm methylacetylene; 40 percent ethylene;
(2) 1.5 ppm acetylene; 990 ppm methylacetylene; 40 percent ethylene; and
(3) 1.5 ppm acetylene; 5140 ppm methylacetylene; 40 percent ethylene.

Results from the analyzers 10 and 31 are used to control the heater 29 of the system 25 by increasing the temperature of the input stream to the hydrogenator 30 to reduce the concentration of acetylene in the output stream from the hydrogenator 30 (provided the concentration of acetylene in the input stream is not excessive) and to reduce the temperature of the input stream to the hydrogenator 30 to prevent thermal run-away of the hydrogenator 30 if the concentration of acetylene in the input stream is excessive.

CONCLUSION

In conclusion, it should be readily apparent that although the invention has been described above in relation with its preferred embodiments, it should be understood that the instant invention is not limited thereby but is intended to cover all alternatives, modifications and equivalents that are included within the scope of the invention as defined by the following claims.

What is claimed is:

1. A chemical analysis method for determining the concentration of at least one gaseous component of interest in a sample gas, comprising the steps of: (a) directing light from a tunable diode laser through an inert gas contained in a sample cell over a selected range of n wavelengths to a light detector to produce a range of baseline signals $I_0 n$ from the light detector, the inert gas being essentially transparent over the selected range of n wavelengths; (b) digitizing the range of baseline signals $I_0 n$ from the light detector; (c) storing the digitized baseline signals $I_0 n$ in a digital computer; (d) directing light from the tunable diode laser through the sample gas contained in the sample cell over the selected range of n wavelengths to the light detector to produce a range of sample signals $I_S n$ from the light detector; (e) digitizing the range of sample signals $I_S n$ from the light detector; (f) storing the digitized sample signals $I_S n$ in a digital computer; (g) calculating a spectrum $I(n)$ in the digital computer according to the equation $I(n)=(I_0 n-I_S n)/I_0 n$; (h) producing a signal from the computer indicative of the concentration of each gaseous component of interest by using spectra of a known concentration of the component of interest in the inert gas stored digitally in the computer, the spectrum of step (g) and a multivariate regression algorithm programmed in the computer, wherein the gaseous components of interest are acetylene and methylacetylene and the sample gas comprises ethylene and methylacetylene from an ethylene cracker hydrogenator, and wherein the pressure in the sample cell is about 100 torr.

2. An apparatus for spectroscopically determining the concentration of at least one gaseous component of interest in a sample gas, the apparatus comprising: (a) a tunable diode laser spectrometer having a digital output signal; (b) a sample cell suitable for containing gaseous samples, and (c) a digital computer for receiving the digital output signal from the spectrometer, the digital computer being programmed to carry out the following functions:
  (a) to receive and store a range of baseline signals $I_0 n$ from the spectrometer produced by directing light from a tunable diode laser through an inert gas contained in the sample cell over a selected range of n wavelengths to a light detector, wherein the inert gas is essentially transparent over the selected range of n wavelengths;
  (b) to receive and store a range of n corresponding sample signals $I_S n$ produced by directing light from the tunable diode laser through a sample gas contained in the sample cell to the light detector over the selected range of n wavelengths;
  (c) to calculate a spectrum $I(n)$ from the stored signals, according to the equation $I(n)=I_0 n-I_S n)/I_0 n$, and thereby
  (d) to compare said spectrum with a spectrum of a known concentration of each component of interest in the inert gas stored digitally in the computer, using a multivariate regression algorithm, to produce a signal indicative of the concentration of the component of interest in the sample gas, wherein the components of interest are acetylene and methylacetylene and the sample gas comprises ethylene and methylacetylene from an ethylene cracker hydrogenator, and wherein the pressure in the sample cell is about 100 torr.

3. The apparatus of claim 2, wherein the sample cell is an off-axis integrated cavity output sample cell.

4. The apparatus of claim 3, further comprising a vacuum pump in fluid communication with the off-axis integrated cavity output sample cell so that the pressure of a gas introduced into the sample cell can be reduced.

* * * * *